(12) United States Patent
Ralph et al.

(10) Patent No.: US 7,094,242 B2
(45) Date of Patent: Aug. 22, 2006

(54) POLYAXIAL DRILL GUIDE

(75) Inventors: James D. Ralph, Seaside Park, NJ (US); Thomas N. Troxell, Pottstown, PA (US)

(73) Assignee: K2M, Inc., Leesburg, VA (US)

( * ) Notice: Subject to any disclaimer, the term of this patent is extended or adjusted under 35 U.S.C. 154(b) by 679 days.

(21) Appl. No.: 10/001,078

(22) Filed: Oct. 31, 2001

(65) Prior Publication Data

US 2003/0083667 A1    May 1, 2003

(51) Int. Cl.
*A61B 17/58* (2006.01)
(52) U.S. Cl. ...................................... 606/96
(58) Field of Classification Search .............. 606/96, 606/80, 82, 98, 97
See application file for complete search history.

(56) References Cited

U.S. PATENT DOCUMENTS 4,632,100 A * 12/1986 Somers et al. ............... 606/73
5,207,679 A * 5/1993 Li .............................. 606/72
5,411,523 A * 5/1995 Goble ......................... 606/232
5,584,860 A * 12/1996 Goble et al. ................ 606/232
5,968,044 A * 10/1999 Nicholson et al. ........... 606/72

* cited by examiner

*Primary Examiner*—Eduardo C. Robert
*Assistant Examiner*—Jessica R. Baxter
(74) *Attorney, Agent, or Firm*—Perry E. Van Over, Esq.; Manelli Denison & Selter, PLLC

(57) ABSTRACT

A polyaxial drill guide includes a body, a collet and a stem. The collet includes a collet shaft having distal and proximal ends and a longitudinal bore. The body includes a conical bore having narrow and wide ends. The distal end of the collet shaft rotatably mounts within the narrow end of the conical bore, with the collet shaft extending toward the wide end of the conical bore, such that the collet shaft (and consequently the longitudinal bore) can be angled within the conical bore at a plurality of angles. The stem includes a shaft having distal and proximal ends and a longitudinal bore. The distal end of the stem shaft mounts to the proximal end of the collet shaft such that the longitudinal bores are co-linear and a drill bit can be inserted into and rotated within the longitudinal bores during a drilling procedure.

10 Claims, 7 Drawing Sheets

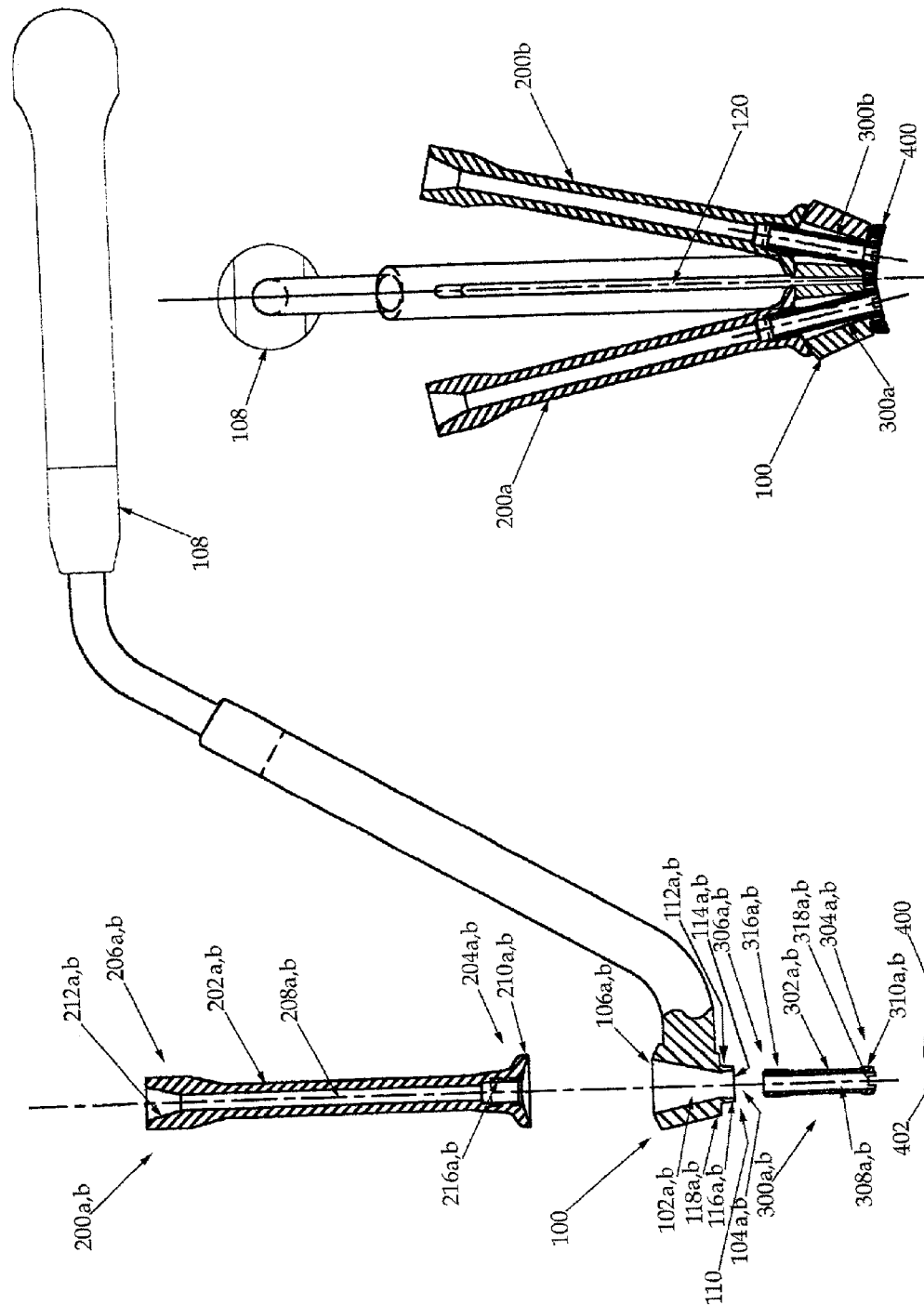

POLYAXIAL DRILL GUIDE

FIELD OF THE INVENTION

This invention relates generally to drill guides and more specifically to a polyaxial drill guide for use in orthopedic surgery.

BACKGROUND OF THE INVENTION

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

Genetic or developmental irregularities, trauma, chronic stress, tumors, and disease are a few of the causes which can result in spinal pathologies for which permanent immobilization of multiple vertebrae may be necessary. A variety of systems have been disclosed in the art that achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back that needs to be immobilized, as well as the individual variations in anatomy, determines the appropriate surgical protocol and implantation assembly. Posterior fixation is much more commonly used in the lower back, i.e., the sacral, lumbar, and lower thoracic regions, than in the upper regions of the thoracic and the cervical spine. The use of screw and plate assemblies for stabilization and immobilization via lateral or anterior entrance in these upper regions is, however, common.

Because the cervical spine is routinely subject to mechanical loads which cycle during movement, one of the primary concerns of physicians performing cervical plate implantation surgeries, as well as of the patients in whom the implants are placed, is the risk of screw pullout. This is of particular concern in the cervical region because of the critical vessels that abut the anterior surfaces of the cervical spine. Screw pullout occurs when the cylindrical portion of the bone that surrounds the inserted screw fails. A bone screw that is implanted perpendicular to the plate is particularly weak because the region of the bone that must fail for pullout to occur is only as large as the outer diameter of the screw threads. It has been found that for pull-out to occur for a pair of screws which are angled inward, "toe nailed", or ones which diverge within the bone, the amount of bone which must fail increases substantially as compared to pairs of screws which are implanted in parallel along the axis that the loading force is applied.

It has, therefore, been an object of those in the art to provide a screw plate assembly that permits the screws to be entered into the vertebral body at angles other than 90 degrees. Certain screw plate assemblies that have been developed fix the angulation of the screw at an angle other than 90 degrees. One such screw plate assembly is the Orion (Reg. Trademark) Anterior Cervical Plate System of Sofamor Danek USA, 1800 Pyramid Place, Memphis, Tenn. 38132. The Orion™ system teaches a plate having two pair of guide holes through which the screws are inserted to fix the plate to the vertebral body. The plate further includes external annular recessions about each of the guide holes that are radially non-symmetric in depth. More particularly, the annular recessions serve as specific angle guides for the screws so that they may be inserted non-perpendicularly with respect to the overall curvature of the plate. Thus, a given plate can accommodate only one screw-in angulation per hole, preferably in accordance with the angle of the annular recession. This is undesirable, in that physicians often must inspect the vertebral bodies during the implantation procedure before making the decision as to which screw-in angle is the ideal. By forcing the physician to chose from a limited set of angles, it is unavoidable that physicians will be forced to implant plates having screws which were positioned non-ideally. While providing a variety of plates having different angle guide holes and annular recession orientations is possible, the complexity and expense of providing a full spectrum of plates available in the operating room for the surgeon to choose from is undesirable. It is a failure of the system that one plate cannot accommodate a variety of different screw-in angles.

Accordingly, other screw plate assemblies that have been developed allow the screws to be angled at a plurality of angles (rather than a single angle) relative to the plate, whereby a single plate is compatible with a wide range of screw-in angles. One such screw plate assembly is the system described in (F-160), which is fully incorporated herein by reference. Using the plate typically involves positioning the plate against the desired vertebral bodies and slidably positioning elongated coupling elements of the assembly in respective elongated through holes in the plate in order to align the entry points for the screws. Next, pre-drilled holes are formed in the vertebral bones at the desired positions and angles, into which the screws are to be inserted. With the plate in place, the screws are inserted through the coupling elements and the through holes, and into the vertebral bodies. As each screw is advanced into the bone, at the desired angle, the semi-spherical head of the screw advances into the interior volume of the coupling element. Continued independent advancement of the screw is prevented by the interference of the relative screw head size and the bottom opening of the coupling element. Continued advancement of the screw, however, causes the coupling element to advance deeper into the tapered through hole. As the tapered surface of the coupling element advances, the lateral constraining forces of the mutual tapers (of the coupling element and the through hole) causes the coupling element to contract slightly as the axial slot or slots are narrowed. This contraction causes the interior volume to crush-lock to the semi-spherical head of the screw thereby locking it at the given angulation and to the plate.

While such a screw plate assembly allows the screws to be angled arbitrarily, it does not assist the surgeon in forming the above-mentioned pre-drilled holes, at desired positions and angles, into which the screws are to be inserted. Accordingly, for use with such screw plate assemblies, and other assemblies within and without the spine industry, there is a need for a drill guide that assists the surgeon in this regard and achieves other desirable results not specifically stated herein.

SUMMARY OF THE INVENTION

The preceding objects of the invention are achieved by the present invention, which is a polyaxial drill guide. Each of the embodiments discussed herein (it should be understood that the present invention is not limited to the discussed embodiments, but rather the embodiments are discussed as examples to illustrate the features of the present invention) provides for the maintaining of drill guide bores adjacent a target area to be drilled, and the ability to angulate the bores during such maintenance so that the drill hole may be drilled at any desired angle within the plurality of angles provided by the particular embodiment. Both single guides and multiple guides are provided; the multiple guides have longitudinal bores that can angulate independently from one another, or dependently on one another via a linking.

A preferred embodiment of the invention includes a drill guide body, a drill guide collet and a drill guide stem. The drill guide collet includes a collet shaft having distal and proximal ends and a longitudinal bore having a diameter that accommodates a drill bit. The drill guide body includes a conical bore having narrow and wide ends. The distal end of the collet shaft rotatably mounts within the narrow end of the conical bore, with the collet shaft extending toward the wide end of the conical bore, such that the collet shaft (and consequently the longitudinal bore) can be angled within the conical bore at a plurality of angles with respect to the major axis of the conical bore. The conical angle of the conical bore establishes the extent to which the collet shaft can be angled.

The rotatable mounting is provided inasmuch as the narrow end of the conical bore has a socket and the distal end of the collet shaft has a semi-spherical outer surface. The semi-spherical outer surface portion seats in the socket and can rotate therein when so fitted. In the preferred embodiment, the walls of the socket have a curvature that matches the contour of the semi-spherical outer surface portion. Also in the preferred embodiment, the semi-spherical outer surface portion can be placed into and removed from the socket via the distal opening of the socket without the application of force. For example, the diameter of the semi-spherical outer surface portion is smaller than the distal opening of the socket. Also in the preferred embodiment, the semi-spherical outer surface portion cannot pass through the interior opening of the socket. For example, the diameter of the semi-spherical outer surface portion is greater than the interior opening of the socket.

The drill guide stem includes a shaft having distal and proximal ends and a longitudinal bore having a diameter that accommodates the drill bit. The distal end of the stem shaft mounts to the proximal end of the collet shaft such that the longitudinal bore of the collet shaft and the longitudinal bore of the stem shaft are co-linear. In the preferred embodiment, this co-linear mounting is provided inasmuch as the longitudinal bore of the stem shaft has at the distal end of the shaft an interior threading and the proximal end of the collet shaft has a corresponding outer threading. Preferably, a recess is provided in the distal end of the collet shaft, for engagement by a tool, such as a screwdriver, to facilitate the attachment of the proximal end of the collet shaft to the distal end of the stem shaft. When the longitudinal bores are co-linear, the drill bit can easily be inserted into and rotated within the longitudinal bores as necessary during a drilling procedure.

In the preferred embodiment, to ensure that the drill guide collet does not slip out of the drill guide body, the distal end of the stem shaft has a conformation that confronts the body near the wide end of the conical bore so as to limit movement of the drill guide stem toward the narrow end of the conical body. In the preferred embodiment, the conformation takes the form of a flange. When the drill guide collet is mounted to the drill guide stem such that the longitudinal bores are co-linear, the flange confronts the drill guide body adjacent the wide end of the conical bore. This confrontation is present regardless of the angulation of the drill guide collet within the conical bore.

The drill guide body has a handle that can be gripped by a surgeon and used to fix the drill guide body in relation to the target area to be drilled, as the drill guide stem is manipulated relative to the drill guide body to angle the longitudinal bore of the collet shaft to a desired drilling angle. In a particular application of the present invention, the fixation of the drill guide body relative to the target area is provided in that the target area to be drilled is below a plate, and the plate includes a hole through which a screw (not shown) is to be screwed into the target area. Accordingly, in the preferred embodiment of the present invention, the drill guide body has a distal end with an outer surface that is formed to rigidly engage the hole of the plate so that the narrow end of the conical bore can be maintained adjacent the target area. This rigid engageability is provided inasmuch as the distal end of the drill guide body has a portion of its outer surface that fits within the hole such that the narrow end of the conical bore is in communication with the target area, and a portion of its outer surface that cannot fit within the hole and prevents passage of the fitting portion through the hole.

In the preferred embodiment, the fitting portion is dimensioned to prevent lateral movement of the fitting portion within the hole. In other embodiments, the distal end of the drill guide body can be formed to enable some lateral movement of the fitting portion 116 within the hole.

Further, the longitudinal bore of the stem shaft has a formation at the proximal end of the stem shaft that facilitates the insertion of a drill bit into the longitudinal bore. This formation is provided in the preferred embodiment inasmuch as the longitudinal bore is outwardly tapered at the proximal end of the drill guide stem shaft so that insertion of the drill bit into the relatively wider tapered end of the longitudinal bore guides the drill bit into the relatively narrower main portion of the longitudinal bore. It should be understood that other formations can be used alternatively to achieve a similar result.

A second embodiment of the present invention is similar to the preferred embodiment, but has a plurality of (in this example, two; it should be understood that more than two can be provided within the scope of the present invention) guide channels (each guide channel being established by a drill guide stem and drill guide collet combination) rather than a single guide channel as in the preferred embodiment. Accordingly, this second embodiment includes a drill guide body, two drill guide stems, and two drill guide collets.

Each of the drill guide collets includes the elements described as part of the collet discussed in the preferred embodiment. The drill guide body includes two conical bores, each having the elements described as part of the conical bore discussed in the preferred embodiment. Each collet shaft distal end rotatably mounts within the associated conical bore narrow end, in the manner described in the preferred embodiment. Each drill guide stem includes the elements described as part of the stem discussed in the preferred embodiment.

The drill guide body has a handle that can be gripped by a surgeon and used to fix the drill guide body in relation to the target areas to be drilled, as each drill guide stem is manipulated relative to the drill guide body to angle each collet shaft longitudinal bore to a respective desired drilling angle. In a particular application of the present invention, the fixation of the drill guide body relative to the target areas is provided in that the target areas to be drilled are below a plate, and the plate includes two holes through which respective screws (not shown) are to be screwed into the respective target areas. Accordingly, in this second embodiment of the present invention, the drill guide body has a distal end with two outer surfaces that are formed to rigidly engage a respective one of the holes of the plate so that the conical bore narrow ends can be maintained adjacent the respective target areas. This rigid engageability is provided for each outer surface in the same manner as in the preferred embodiment.

It should be noted that each conical bore is formed in a respective portion of the drill guide body, and that the portions are movable relative to one another. This enables this embodiment of the present invention to accommodate a variety of hole spacings on plates. For example, one plate with which this embodiment is used may have holes that are spaced apart by a particular distance, whereas another plate with which this embodiment is used may have holes that are slightly closer together, slightly farther apart, or otherwise not in the same configuration as the first plate. Because the portions of the drill guide body are movable relative to one another, the embodiment can adjust to the different plate configurations; this prevents the surgeon from having to use a different drill guide for each plate. In this embodiment, the relative movability is provided inasmuch as the portions of the body are separated from one another by a slot formed in the body. The slot is formed to allow the connected regions of the body to act as a fulcrum point for the portions moving relative to one another about the fulcrum point.

A third embodiment of the invention is similar to the preferred embodiment, but does not use a drill guide stem. The collet shaft is longer than the collet shaft of the preferred embodiment, and the distal end of the collet shaft is ball-shaped and cannot be placed into or removed from the socket without radially compressing the ball-shaped semi-spherical outer surface portion under force. Therefore, the distal end of the collet shaft is maintained in the curvate socket without the use of a stem having flanges as discussed in the preferred embodiment.

More particularly, the rotatable mounting in this third embodiment is provided inasmuch as the walls of the socket have a curvature that matches the contour of the semi-spherical outer surface portion. The semi-spherical outer surface portion cannot be placed into or removed from the curvate socket without the application of force. For example, the socket is curvate (preferably ball-shaped) and the resting diameter of the semi-spherical outer surface portion is greater than the distal opening of the curvate socket and greater than the interior opening of the curvate socket. This prevents the semi-spherical outer surface portion from slipping out of the curvate socket once it is fitted therein.

In order to enable the semi-spherical outer surface portion to be seated in the curvate socket and removed therefrom, the semi-spherical outer surface portion in the third embodiment is formed with a notch that allows the semi-spherical outer surface portion to be radially compressed under pressure to reduce its diameter enough to allow it to be passed through the distal opening of the curvate socket. Once the pressure is released, the semi-spherical outer surface portion returns to its resting diameter. Therefore, a force can be applied to press the semi-spherical outer surface portion through the distal opening of the curvate socket, causing the semi-spherical outer surface portion to radially compress enough to pass through the distal opening. Once through the distal opening, the radially pressure is alleviated and the semi-spherical outer surface portion returns to its resting diameter, and therefore it is secured loosely within the curvate socket to that it can rotate therein without slipping out.

A fourth embodiment of the present invention is similar to the third embodiment, but has a plurality of (in this example, two; it should be understood that more than two can be provided within the scope of the present invention) guide channels (each guide channel being established by a drill guide stem and drill guide collet combination) rather than a single guide channel as in the third embodiment. Accordingly, this fourth embodiment includes a drill guide body and two drill guide collets.

Each of the drill guide collets includes the elements described as part of the collet discussed in the third embodiment. The drill guide body includes two conical bores, each having the elements described as part of the conical bore discussed in the third embodiment. Each collet shaft distal end rotatably mounts within the associated conical bore narrow end, in the manner described in the third embodiment.

The drill guide body has a handle that can be gripped by a surgeon and used to fix the drill guide body in relation to the target areas to be drilled, as each drill guide stem is manipulated relative to the drill guide body to angle each collet shaft longitudinal bore to a respective desired drilling angle. In a particular application of the present invention, the fixation of the drill guide body relative to the target areas is provided in that the target areas to be drilled are below a plate, and the plate includes two holes through which respective screws (not shown) are to be screwed into the respective target areas. Accordingly, in this fourth embodiment of the present invention, the drill guide body has a distal end with two outer surfaces that are formed to rigidly engage a respective one of the holes of the plate so that the conical bore narrow ends can be maintained adjacent the respective target areas. This rigid engageability is provided for each outer surface in the same manner as in the third embodiment.

It should be noted that each conical bore is formed in a respective portion of the drill guide body, and that the portions are movable relative to one another. This enables this embodiment of the present invention to accommodate a variety of hole spacings on plates. For example, one plate with which this embodiment is used may have holes that are spaced apart by a particular distance, whereas another plate with which this embodiment is used may have holes that are slightly closer together, slightly farther apart, or otherwise not in the same configuration as the first plate. Because the portions of the drill guide body are movable relative to one another, the embodiment can adjust to the different plate configurations; this prevents the surgeon from having to use a different drill guide for each plate. In this embodiment, the relative movability is provided inasmuch as the portions of the body are separated from one another by a slot formed in the body. The slot is formed to allow the connected regions of the body to act as a fulcrum point for the portions moving relative to one another about the fulcrum point.

In some embodiments having multiple drill guides, at least two of the guide members are linked for mutual relative angular movement. For example, in some embodiments, a mechanical link between two guide members enables an operator of the drill guide (typically a surgeon) to increase or decrease the angle between the guide members. This is useful for ensuring that the angle of each guide member relative to the drill guide body is roughly equivalent to the angle of the other guide member relative to the drill guide body. Preferably, when it is desirable for the guide members to be angled independently, the mechanical link can be disengaged fully from the guide members. The embodiment illustrated in these respects herein shows a turnbuckle as a mechanical link.

BRIEF DESCRIPTION OF THE DRAWINGS

FIG. 2a is a side exploded view of a second embodiment of the present invention, showing a dual polyaxial drill guide having a drill guide body, two drill guide collets (one collet is behind the other in this view), and two drill guide stems (one stem is behind the other in this view).

FIG. 2b is a front assembled view of the second embodiment of the present invention, engaging a cervical plate, with each co-linear drill guide collet longitudinal bore and drill guide stem longitudinal bore coaxial with a respective conical bore of the drill guide body.

DETAILED DESCRIPTION OF THE PREFERRED EMBODIMENT

While the present invention will be described more fully hereinafter with reference to the accompanying drawings, in which particular embodiments are shown, it is to be understood at the outset that persons skilled in the art may modify the invention herein described while achieving the functions and results of this invention. Accordingly, the descriptions that follow are to be understood as illustrative and exemplary of specific structures, aspects and features within the broad scope of the present invention and not as limiting of such broad scope. Like numbers refer to similar features of like elements throughout.

Figure 1A:
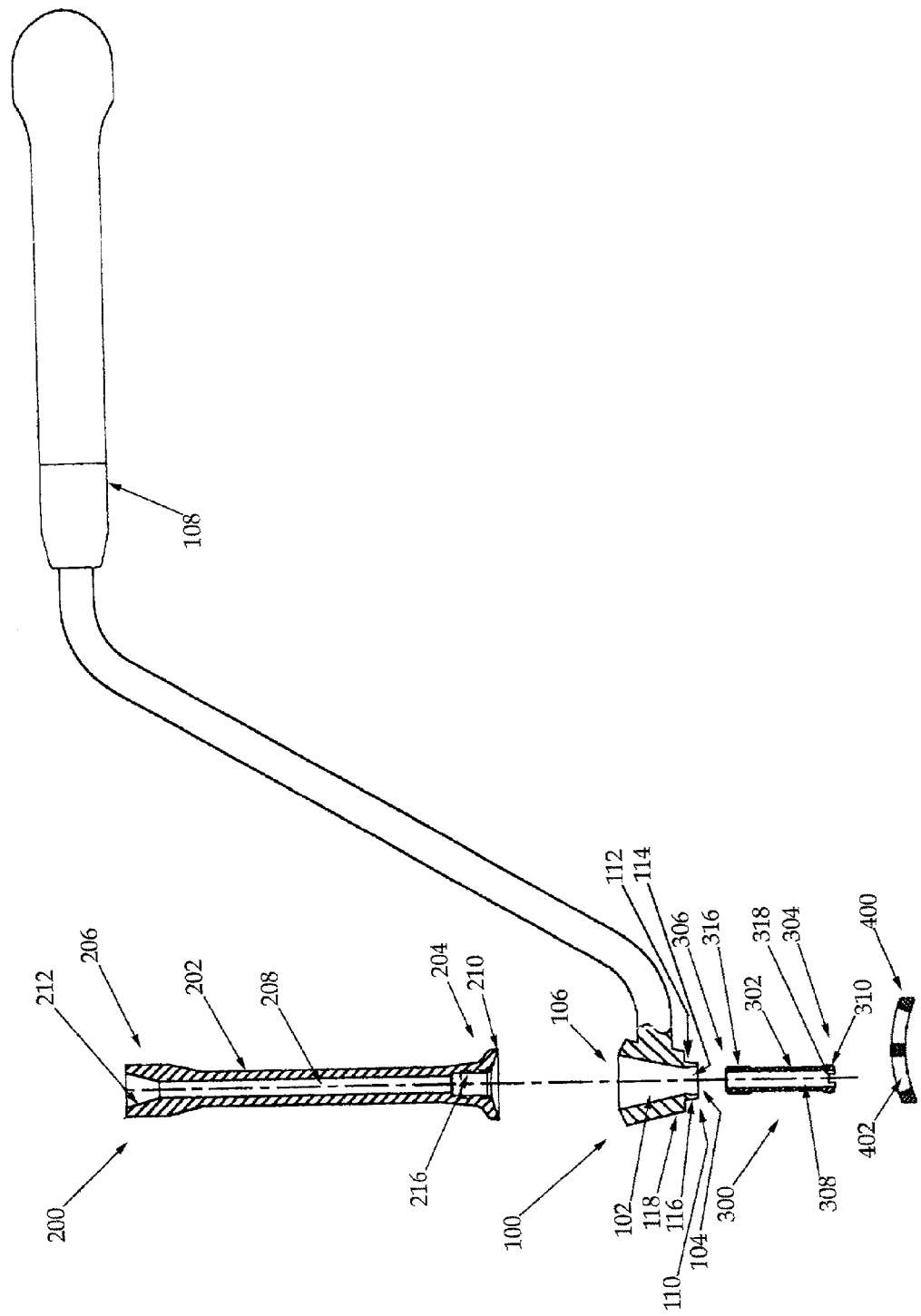
FIG. 1a is a side exploded view of a preferred embodiment of the present invention, showing a single polyaxial drill guide having a drill guide body, a drill guide collet, and a drill guide stem.
Figure 1C:
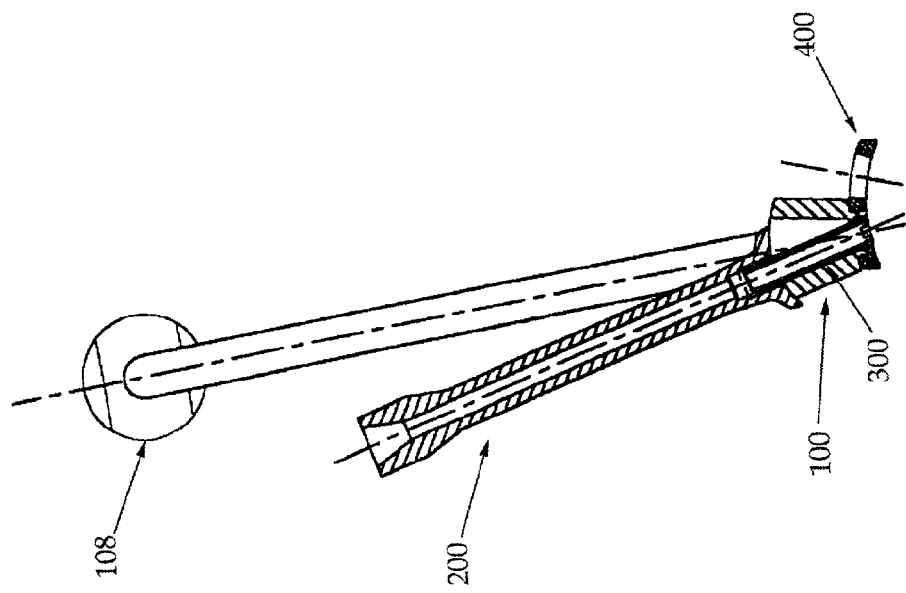
FIG. 1c is a front assembled view of the preferred embodiment of the present invention, engaging a cervical plate, with the longitudinal bores of the drill guide collet and the drill guide stem angled with respect to the axis of the conical bore of the drill guide body.
Figure 1B:
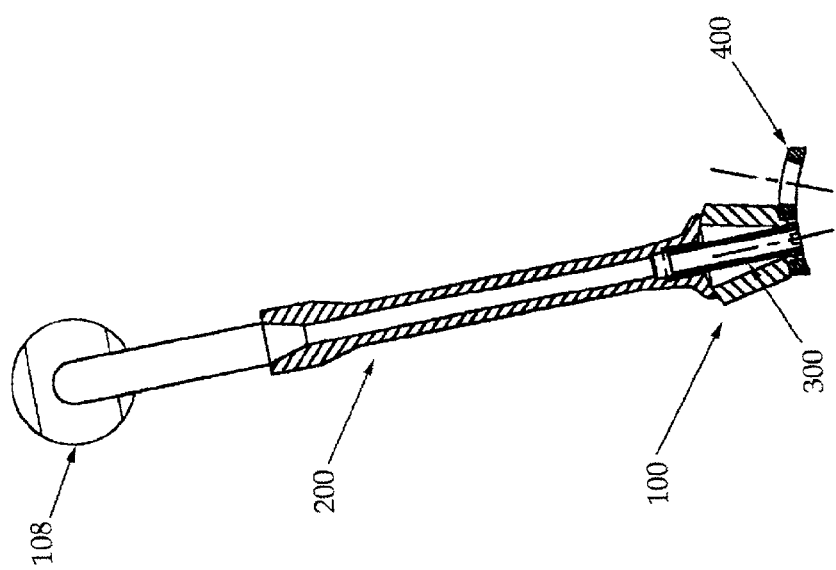
FIG. 1b is a front assembled view of the preferred embodiment of the present invention, engaging a cervical plate, with the longitudinal bores of the drill guide collet and the drill guide stem coaxial with the conical bore of the drill guide body.

Referring now to FIGS. 1a–c, a preferred embodiment of the invention includes a drill guide body 100, a drill guide collet 300 (also referred to herein as a guide member) and a drill guide stem 200 (also referred to herein as an extension member).

The drill guide collet 300 includes a collet shaft 302 having distal and proximal ends 304, 306 and a longitudinal bore 308 having a diameter that accommodates a drill bit. The drill guide body 100 includes a conical bore 102 having narrow and wide ends 104, 106. The distal end 304 of the collet shaft 302 rotatably mounts within the narrow end 104 of the conical bore 102, with the collet shaft 302 extending toward the wide end 106 of the conical bore 102, such that the collet shaft 302 (and consequently the longitudinal bore 308) can be angled within the conical bore 102 at a plurality of angles with respect to the major axis of the conical bore 102. The conical angle of the conical bore 102 establishes the extent to which the collet shaft 302 can be angled.

The rotatable mounting is provided inasmuch as the narrow end 104 of the conical bore 102 has a socket 114 and the distal end 304 of the collet shaft 302 has a semi-spherical outer surface 310. The semi-spherical outer surface portion 310 seats in the socket 114 and can rotate therein when so fitted. In the preferred embodiment, the walls of the socket 114 have a curvature that matches the contour of the semi-spherical outer surface portion 310; however, it should be understood that in other embodiments, walls of other types can be used, such as, for example, walls without a curvature and walls having a different curvature. Also in the preferred embodiment, the semi-spherical outer surface portion 310 can be placed into and removed from the socket 114 via the distal opening of the socket 114 without the application of force. For example, the diameter of the semi-spherical outer surface portion 310 is smaller than the distal opening of the socket 114. Also in the preferred embodiment, the semi-spherical outer surface portion 310 cannot pass through the interior opening (also referred to herein as the proximal opening) of the socket 114. For example, the diameter of the semi-spherical outer surface portion 310 is greater than the interior opening of the socket 114.

The drill guide stem 200 includes a shaft 202 having distal and proximal ends 204, 206 and a longitudinal bore 208 having a diameter that accommodates the drill bit. The distal end 204 of the stem shaft 202 mounts to the proximal end 306 of the collet shaft 302 such that the longitudinal bore 308 of the collet shaft 302 and the longitudinal bore 208 of the stem shaft 202 are co-linear. In the preferred embodiment, this co-linear mounting is provided inasmuch as the longitudinal bore 208 of the stem shaft 202 has at the distal end 204 of the shaft 202 an interior threading 216 and the proximal end 306 of the collet shaft 302 has a corresponding outer threading 316. The inner threading 216 matches the outer threading 316 so that the threadings are mutually engageable. When the proximal end 306 of the collet shaft 302 is screwed into the distal end 204 of the stem shaft 202, the longitudinal bores 208, 308 are fixed together in co-linear relation. Preferably, this threaded interface is a locking thread interface of a type known in the art, for example, the Spirol™ locking thread interface. Also preferably, a recess 218 is provided in the distal end 304 of the collet shaft 302, for engagement by a tool, such as a screwdriver, to facilitate the attachment of the proximal end 306 of the collet shaft 302 to the distal end 204 of the stem shaft 202.

When the longitudinal bores 208, 308 are co-linear, the drill bit can easily be inserted into and rotated within the longitudinal bores 208, 308 as necessary during a drilling procedure.

In the preferred embodiment, to ensure that the drill guide collet 300 does not slip out of the drill guide body 100 (as discussed above, in the preferred embodiment, the semi-spherical outer surface portion 310 can be placed into and removed from the socket 114 via the distal opening without the application of force; therefore, it may fall out unless prevented from doing so), the distal end 204 of the stem shaft 202 has a conformation that confronts the body 100 near the wide end 106 of the conical bore 102 so as to limit movement of the drill guide stem 200 toward the narrow end 104 of the conical body 102. In the preferred embodiment, the conformation takes the form of a flange 210 (it should be understood that in other embodiments, the conformation make take other forms). When the drill guide collet 300 is mounted to the drill guide stem 200 such that the longitudinal bores 208, 308 are co-linear (as described in the previous paragraph), the flange 210 confronts the drill guide body 100 adjacent the wide end 106 of the conical bore 102. This confrontation is present regardless of the angulation of the drill guide collet 300 within the conical bore 102. Stated alternatively, the semi-spherical outer surface portion 310 of the drill guide collet 300 cannot slip out of the socket 114 in the assembled preferred embodiment because the flange 210 prevents such movement. It should be noted that the semi-spherical outer surface portion 310 of the drill guide collet 300 also cannot slip through the interior opening of the socket 114 in the assembled preferred embodiment because the diameter of the semi-spherical outer surface portion 310 is greater than the width of the interior opening of the socket 114. It should also be noted that tightening and loosening of the threaded interface (between the collet proximal end 306 and the stem distal end 204) tightens and loosens the fits of the collets 300 in the conical bore 102 (stated alternatively, adjusts the distances between the flange 210 and the semi-spherical outer surface portion 310); this is useful in that the gliding of the collet 300 in the sockets (during adjustment of the angle of longitudinal bore 308) can be made easier or more difficult, depending on the preference of the operator of the drill guide.

The drill guide body 100 has a handle 108 that can be gripped by a surgeon and used to fix the drill guide body 100 in relation to the target area to be drilled, as the drill guide stem 200 is manipulated relative to the drill guide body 100 to angle the longitudinal bore 308 of the collet shaft 302 to a desired drilling angle. In the illustrated example, the fixation of the drill guide body 100 relative to the target area is provided in that the target area to be drilled is below a plate 400, and the plate 400 includes a hole 402 through which a screw (not shown) is to be screwed into the target area. Accordingly, in the preferred embodiment of the present invention, the drill guide body 100 has a distal end 110 with an outer surface 112 that is formed to rigidly engage the hole 402 of the plate 400 so that the narrow end 104 of the conical bore 102 can be maintained adjacent the target area. This rigid engageability is provided inasmuch as the distal end 110 of the drill guide body 100 has a portion 116 of its outer surface 112 that fits within the hole 402 such that the narrow end 104 of the conical bore 102 is in communication with the target area, and a portion 118 of its outer surface 112 that cannot fit within the hole 402 and prevents passage of the fitting portion 116 through the hole 402.

In the preferred embodiment, the fitting portion 116 is dimensioned to prevent lateral movement of the fitting portion 116 within the hole 402. It should be noted that the present invention can be adapted for use with any hole formation, including circular, oblong, square, rectangular, or other shaped holes. Further, the distal end 110 of the drill guide body 100 can be formed to match the shape of the particular hole, with the fitting portion 116 having dimensions slightly smaller than the hole dimensions (so that it can fit within the hole with limited or no lateral movement therein), and the non-fitting portion 118 having dimensions greater than the hole dimensions. For example, in the case of a circular hole having a hole diameter, the outer surface 112 of the distal end 110 of the drill guide body 100 would have an annular recess establishing a diameter of the fitting portion 116 that is slightly smaller than the hole diameter, and a diameter of the non-fitting potion 118 that is larger than the hole diameter. Or, for example, in the case of an oblong hole (or other shaped hole), the outer surface 112 of the distal end 110 of the drill guide body 100 would have a recess shaped to establish a shape of the fitting portion 116 that matches the shape of the hole (but slightly smaller so that it fits in the hole), and to establish at least one dimension of the non-fitting portion 118 that is larger than a corresponding dimension of the hole.

In other embodiments, the distal end 110 of the drill guide body 100 can be formed to enable some lateral movement of the fitting portion 116 within the hole 402. Such embodiments can be used where the hole presents not one target area, but rather a region presenting many possible target areas. For example, the hole 402 can be an oblong hole having a particular length, and the fitting portion 116 can be formed to have the dimensions of a circle fitting within the oblong hole, or the dimensions of an oval fitting within the oblong hole (but with a length shorter than the length of the oblong hole). Such a fitting portion 116 formation would enable the fitting portion 116 to be moved laterally within the hole 402, along the length of the oblong hole, so that even after the plate 400 is held in place, further determinations can be made as to the desirable place for the drill hole. Particular formations of the hole edges and/or the fitting portion edges can be used to ease the lateral movement; such formations can be tracks, rails, or the like. Lateral movement in more than one linear axis can be achieved as well, using, for example, cross-shaped holes, t-shaped holes, or holes having tracks or grids spanning the hole and upon which the fitting portion rides to be placed in a plurality of positions.

Further, the longitudinal bore 208 of the stem shaft 202 has a formation 212 at the proximal end 206 of the stem shaft 202 that facilitates the insertion of a drill bit into the longitudinal bore 208. This formation 212 is provided in the preferred embodiment inasmuch as the longitudinal bore 208 is outwardly tapered at the proximal end 206 of the drill guide stem shaft 202 so that insertion of the drill bit into the relatively wider tapered end of the longitudinal bore 208 guides the drill bit into the relatively narrower main portion of the longitudinal bore 208. It should be understood that other formations can be used alternatively to achieve a similar result.

Referring now to FIGS. 2a–b, a second embodiment of the present invention is shown as similar to the preferred embodiment, but having a plurality of (in this example, two; it should be understood that more than two can be provided within the scope of the present invention) guide channels (each guide channel being established by a drill guide stem and drill guide collet combination) rather than a single guide channel as in the preferred embodiment. Accordingly, this second embodiment includes a drill guide body 100, two drill guide stems 200a, 200b (also referred to herein as extension members), and two drill guide collets 300a, 300b (also referred to herein as guide members).

Each of the drill guide collets 300a, 300b includes a collet shaft 302a, 302b having a distal end 304a, 304b and a proximal end 306a, 306b and a longitudinal bore 308a, 308b having a diameter that accommodates a drill bit. The drill guide body 100 includes two conical bores 102a, 102b, each having a narrow end 104a, 104b and a wide end 106a, 106b. Each collet shaft distal end 304a, 304b rotatably mounts within the associated conical bore narrow end 104a, 104b, with its collet shaft 302a, 302b extending toward the associated conical bore wide end 106a, 106b, such that its collet shaft 302a, 302b (and consequently the associated longitudinal bore 308a, 308b) can be angled within the associated conical bore 102a, 102b at a plurality of angles with respect to the major axis of the associated conical bore 102a, 102b. The conical angle of each conical bore 102a, 102b establishes the extent to which the associated collet shaft 302a, 302b can be angled.

The rotatable mounting is provided inasmuch as each conical bore narrow end 104a, 104b has a socket 114a, 114b and each collet shaft distal end 304a, 304b has a semi-spherical outer surface 310a, 310b. Each semi-spherical outer surface portion 310a, 310b seats within the associated socket 114a, 114b and can rotate therein when so fitted. In this second embodiment, the walls of each socket 114a, 114b have a curvature that matches the contour of the associated semi-spherical outer surface portion 310a, 310b; however, it should be understood that in other embodiments, walls of other types can be used, such as, for example, walls without a curvature and walls having a different curvature. Also in this second embodiment, each semi-spherical outer surface portion 310a, 310b can be placed into and removed from the associated socket 114a, 114b via the distal opening of the socket without the application of force. For example, the diameter of each semi-spherical outer surface portion 310a, 310b is smaller than the distal opening of the associated socket 114a, 114b. Also in this second embodiment, neither semi-spherical outer surface portion 310a, 310b can pass through the interior opening (also referred to herein as the proximal opening) of the associated socket 114a, 114b. For example, the diameter of each semi-spherical outer surface portion 310a, 310b is greater than the interior opening of the associated socket 114a, 114b.

Each drill guide stem 200a, 200b includes a shaft 202a, 202b having a distal end 204a, 204b and a proximal end 206a, 206b and a longitudinal bore 208a, 208b having a diameter that accommodates the drill bit. Each stem shaft distal end 204a, 204b mounts to the associated collet shaft proximal end 306a, 306b such that each collet shaft longitudinal bore 308a, 308b is co-linear with the associated stem shaft longitudinal bore 208a, 208b. In this second embodiment, this co-linear mounting is provided inasmuch as each stem shaft longitudinal bore 208a, 208b has at the associated stem shaft distal end 204a, 204b an interior threading 216a, 216b and the associated collet shaft proximal end 306a, 306b has a corresponding outer threading 316a, 316b. Each inner threading 216a, 216b matches the corresponding outer threading 316a, 316b so that the threadings are mutually engageable. When each collet shaft proximal end 306a, 306b is screwed into the associated stem shaft distal end 204a, 204b, the longitudinal bores 208a and 308a are fixed together in co-linear relation, and the longitudinal bores 208b and 308b are fixed together in co-linear relation. Preferably, this threaded interface is a locking threaded interface of a type known in the art, for example, the Spirol™ locking thread interface. Also preferably, a respective recess 218a, 218b is provided in each collet shaft distal end 304a, 304b, for engagement by a tool, such as a screwdriver, to facilitate the attachment of each collet shaft proximal end 306a, 306b to the associated stem shaft distal end 204.

When the longitudinal bores 208a and 308a are co-linear, the drill bit can easily be inserted into and rotated within the longitudinal bores 208a and 308a as necessary during a drilling procedure. Similarly, when the longitudinal bores 208b and 308b are co-linear, the drill bit can easily be inserted into and rotated within the longitudinal bores 208b and 308b as necessary during a drilling procedure.

In this second embodiment, as in the preferred embodiment, to ensure that the drill guide collets 300a, 300b do not slip out of the drill guide body 100 (as discussed above, in this second embodiment, each semi-spherical outer surface portion 310a, 310b can be placed into and removed from the associated socket 114a, 114b via the distal opening of the socket without the application of force; therefore, it may fall out unless prevented from doing so), each stem shaft distal end 204a, 204b has a conformation that confronts the body 100 near the associated conical bore wide end 106a, 106b so as to limit movement of the associated drill guide stem 200a, 200b toward the associated conical bore narrow end 104a, 104b. In this second embodiment, each conformation takes the form of a flange 210a, 210b (it should be understood that in other embodiments, the conformations make take other forms). When the drill guide collets 300a, 300b are mounted to the associated drill guide stems 200a, 200b such that the longitudinal bores 208a, 308a are co-linear and the longitudinal bores 208b, 308b are co-linear (as described in the previous paragraph), each flange 210a, 210b confronts the drill guide body 100 adjacent the associated conical bore wide end 106a, 106b. The confrontations are present regardless of the angulation of the associated drill guide collet 300a, 300b within the associated conical bore 102a, 102b. Stated alternatively, the semi-spherical outer surface portion 310a, 310b of each drill guide collet 300a, 300b cannot slip out of the associated socket 114a, 114b in the assembled second embodiment because the associated flange 210a, 210b prevents such longitudinal movement. It should be noted that the semi-spherical outer surface portion 310a, 310b of each drill guide collet 300a, 300b also cannot slip through the interior opening of the associated socket 114a, 114b in the assembled second embodiment because the diameter of the semi-spherical outer surface portion 310a, 310b is greater than the width of the interior opening of the associated socket 114a, 114b. It should also be noted that tightening and loosening of the threaded interfaces (between the collet proximal ends 306a, 306b and the stem distal ends 204a, 204b) tightens and loosens the fits of the collets 300a, 300b in the conical bores 102a, 102b (stated alternatively, adjusts the distances between the flanges 210a, 210b and the semi-spherical outer surface portions 310a, 310b); this is useful in that the gliding of the collets 300*a*, 300*b* in the sockets (during adjustment of the angle of longitudinal bores 308*a*, 308*b*) can be made easier or more difficult, depending on the preference of the operator of the drill guide.

The drill guide body 100 has a handle 108 that can be gripped by a surgeon and used to fix the drill guide body 100 in relation to the target areas to be drilled, as each drill guide stem 200*a*, 200*b* is manipulated relative to the drill guide body 100 to angle each collet shaft longitudinal bore 308*a*, 308*b* to a respective desired drilling angle. In the illustrated example, the fixation of the drill guide body 100 relative to the target areas is provided in that the target areas to be drilled are below a plate 400, and the plate 400 includes two holes 402*a*, 402*b* through which respective screws (not shown) are to be screwed into the respective target areas. Accordingly, in this second embodiment of the present invention, the drill guide body 100 has a distal end 110 with two outer surfaces 112*a*, 112*b* that are formed to rigidly engage a respective one of the holes 402*a*, 402*b* of the plate 400 so that the conical bore narrow ends 104*a*, 104*b* can be maintained adjacent the respective target areas. This rigid engageability is provided inasmuch as each of the distal end outer surfaces 112*a*, 112*b* has a portion 116*a*, 116*b* that fits within the respective one of the holes 402*a*, 402*b* such that the associated conical bore narrow end 104*a*, 104*b* is in communication with the respective target area, and a portion 118*a*, 118*b* that cannot fit within the respective one of the holes 402*a*, 402*b* and prevents passage of the fitting portions 116*a*, 116*b* through the respective one of the holes 402*a*, 402*b*.

Preferably, as shown, each fitting portion 116*a*, 116*b* is dimensioned to prevent lateral movement thereof within the respective hole 402*a*, 402*b*. It should be noted that the present invention can be adapted for use with any hole formation, including circular, oblong, square, rectangular, or other shaped holes. Further, the distal end 110 of the drill guide body 100 can be formed to match the shape of the particular hole, with each fitting portion 116*a*, 116*b* having dimensions slightly smaller than the respective hole dimensions (so that it can fit within the hole with limited or no lateral movement therein), and each non-fitting portion 118*a*, 118*b* having dimensions greater than the respective hole dimensions. For example, in the case of a circular hole having a hole diameter, each distal end outer surface 112*a*, 112*b* would have an annular recess establishing a diameter of the associated fitting portion 116*a*, 116*b* that is slightly smaller than the respective hole diameter, and a diameter of the associated non-fitting potion 118*a*, 118*b* that is larger than the respective hole diameter. Or, for example, in the case of an oblong hole (or other shaped hole), each distal end outer surface 112*a*, 112*b* would have a recess shaped to establish the shape of each fitting portion 116*a*, 116*b* that matches the shape of the respective hole (but slightly smaller so that it fits in the hole), and to establish at least one dimension of each non-fitting portion 118*a*, 118*b* that is larger than a corresponding dimension of the respective hole 402*a*, 402*b*.

In other embodiments, the distal end 110 of the drill guide body 100 can be formed to enable some lateral movement of one or more of the fitting portions 116*a*, 116*b* within the associated hole 402*a*, 402*b*. Such embodiments can be used where one or more of the holes presents not one target area, but rather a region presenting many possible target areas. For example, one or more of the holes can be an oblong hole having a particular length, and the associated fitting portion can be formed to have the dimensions of a circle fitting within the oblong hole, or the dimensions of an oval fitting within the oblong hole (but with a length shorter than the length of the oblong hole). Such a fitting portion formation would enable the fitting portion to be moved laterally within the hole, along the length of the oblong hole, so that even after the plate is held in place, further determinations can be made as to the desirable place for the drill hole. Particular formations of the hole edges and/or the fitting portion edges can be used to ease the lateral movement; such formations can be tracks, rails, or the like. Lateral movement in more than one linear axis can be achieved as well, using, for example, cross-shaped holes, t-shaped holes, or holes having tracks or grids spanning the hole and upon which the fitting portion rides to be placed in a plurality of positions.

It should be noted that each conical bore 102*a*, 102*b* is formed in a respective portion of the drill guide body 100, and that the portions are movable relative to one another. This enables this embodiment of the present invention to accommodate a variety of hole spacings on plates. For example, one plate with which this embodiment is used may have holes that are spaced apart by a particular distance, whereas another plate with which this embodiment is used may have holes that are slightly closer together, slightly farther apart, or otherwise not in the same configuration as the first plate. Because the portions of the drill guide body 100 are movable relative to one another, the embodiment can adjust to the different plate configurations; this prevents the surgeon from having to use a different drill guide for each plate. In this embodiment, the relative movability is provided inasmuch as the portions of the body are separated from one another by a slot 120 formed in the body. The slot 120 is formed to allow the connected regions of the body to act as a fulcrum point for the portions moving relative to one another about the fulcrum point. It should be understood that the relative movability can be provided in other ways without departing from the scope of the invention, including through the use of hinges, joints, and the like. It should also be understood that if more than two portions are required to be made movable relative to one another, that additional slots (or hinges, or joints, or the like) can be provided in the drill guide body 100 to effect this.

Further, each stem shaft longitudinal bore 208*a*, 208*b* has a formation 212*a*, 212*b* at the stem shaft proximal end 206*a*, 206*b* that facilitates the insertion of a drill bit into the longitudinal bore 208*a*, 208*b*. Each formation 212*a*, 212*b* is provided inasmuch as the associated longitudinal bore 208*a*, 208*b* is outwardly tapered at the associated stem shaft proximal end 206*a*, 206*b* so that insertion of the drill bit into either longitudinal bore's relatively wider tapered end guides the drill bit into the relatively narrower main portion of the associated longitudinal bore 208*a*, 208*b*. It should be understood that other formations can be used alternatively to achieve a similar result.

Figure 3A:
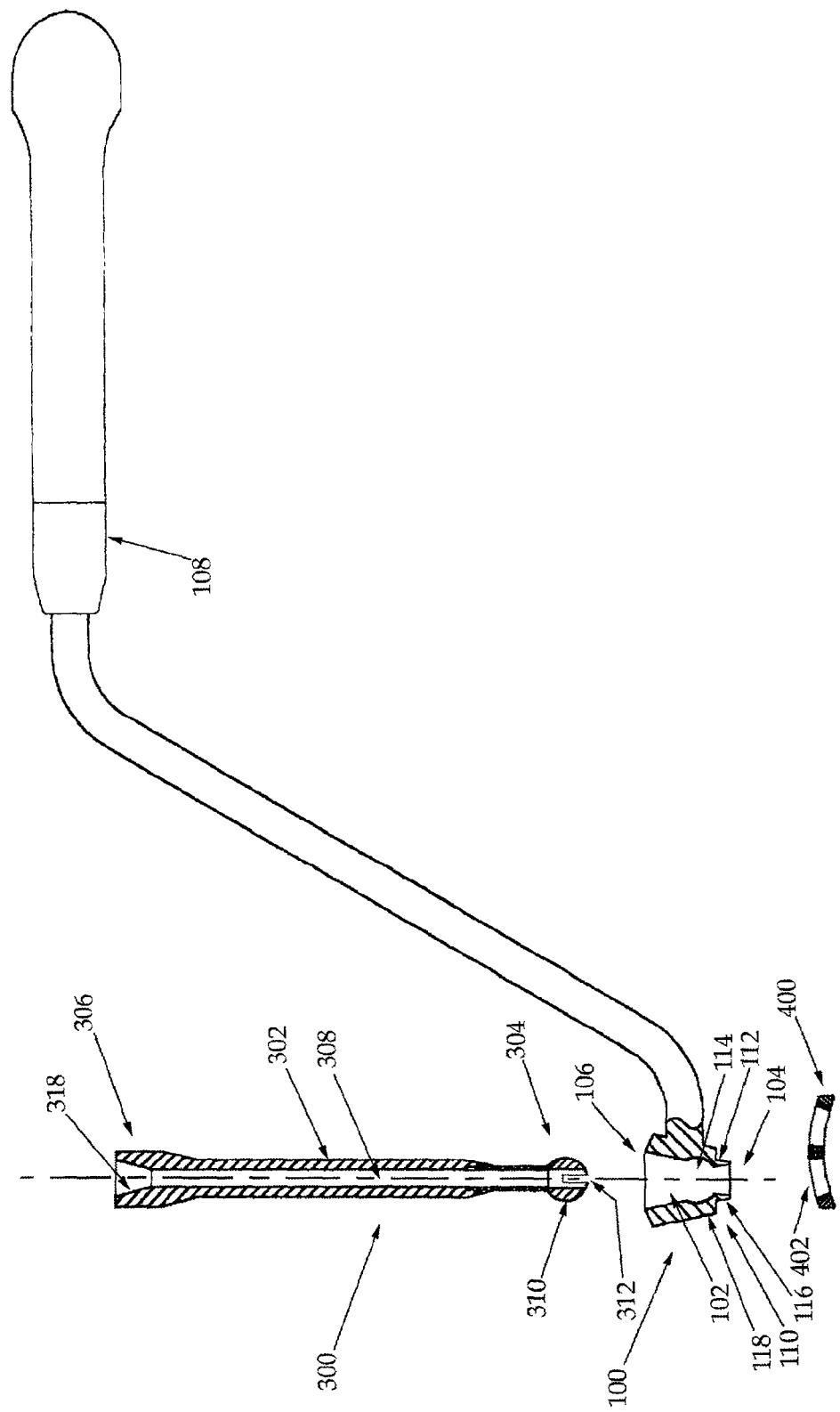
FIG. 3a is a side exploded view of a third embodiment of the present invention, showing a single polyaxial drill guide having a drill guide body with a curvate socket and a drill guide collet with a curvate head.
Figure 3C:
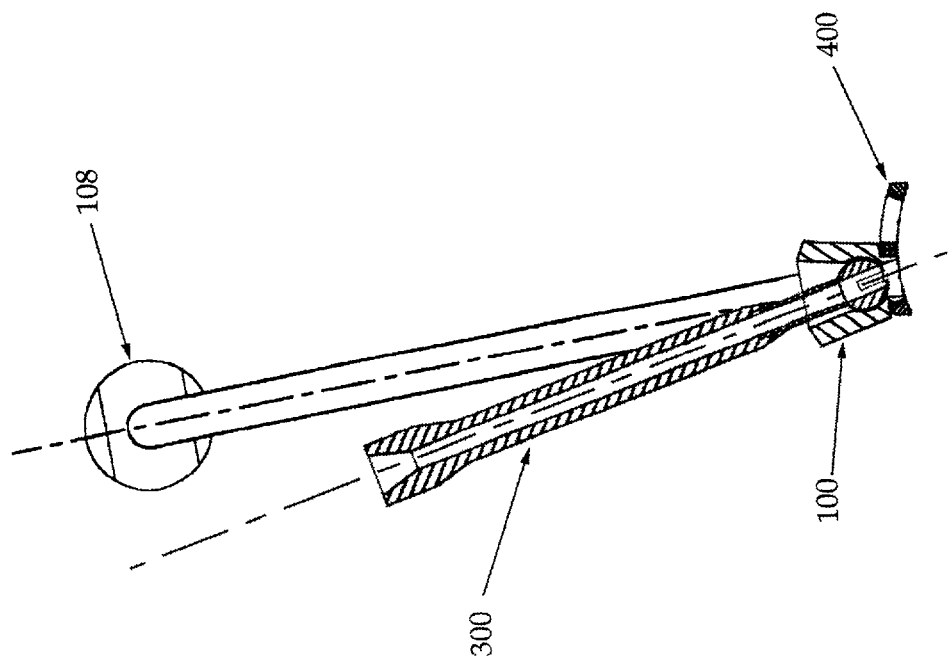
FIG. 3c is a front assembled view of the third embodiment of the present invention, engaging a cervical plate, with the longitudinal bore of the drill guide collet angled with respect to the axis of the conical bore of the drill guide body.
Figure 3B:
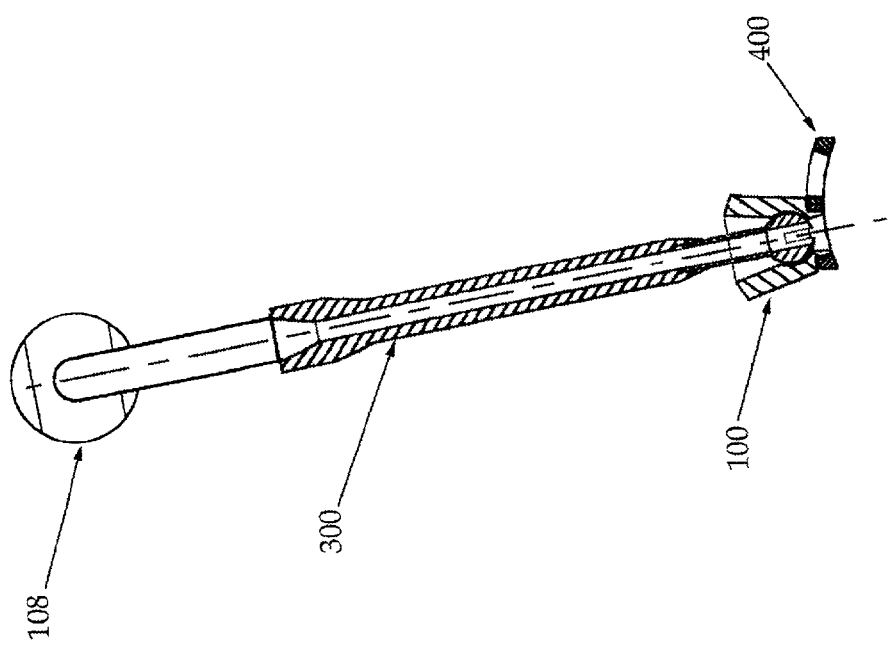
FIG. 3b is a front assembled view of the third embodiment of the present invention, engaging a cervical plate, with the longitudinal bore of the drill guide collet coaxial with the conical bore of the drill guide body.

Referring now to FIGS. 3*a–c*, a third embodiment of the invention includes a drill guide body 100 and a drill guide collet 300 (also referred to herein as a guide member).

The drill guide collet 300 includes a collet shaft 302 having distal and proximal ends 304, 306 and a longitudinal bore 308 having a diameter that accommodates a drill bit. The drill guide body 100 includes a conical bore 102 having narrow and wide ends 104, 106. The distal end 304 of the collet shaft 302 rotatably mounts within the narrow end 104 of the conical bore 102, with the collet shaft 302 extending toward the wide end 106 of the conical bore 102, such that the collet shaft 302 (and consequently the longitudinal bore 308) can be angled within the conical bore 102 at a plurality of angles with respect to the major axis of the conical bore 102. The conical angle of the conical bore 102 establishes the extent to which the collet shaft 302 can be angled.

The rotatable mounting is provided inasmuch as the narrow end 104 of the conical bore 102 has a socket 114 and the distal end 304 of the collet shaft 302 has a semi-spherical outer surface 310. The semi-spherical outer surface portion 310 seats within the socket 114 and can rotate therein when so fitted. In this third embodiment, the walls of the socket 114 have a curvature that matches the contour of the semi-spherical outer surface portion 310; however, it should be understood that in other embodiments, walls of other types can be used, such as, for example, walls having a different curvature. Also in this third embodiment, the semi-spherical outer surface portion 310 cannot be placed into or removed from the curvate socket 114 without the application of force. For example, the socket 114 is curvate (preferably, as shown, ball-shaped) and the resting diameter of the semi-spherical outer surface portion 310 is greater than the distal opening of the curvate socket 114 and greater than the interior opening (also referred to herein as the proximal opening) of the curvate socket 114. This prevents the semi-spherical outer surface portion 310 from slipping out of the curvate socket 114 once it is fitted therein.

In order to enable the semi-spherical outer surface portion 310 to be seated in the curvate socket 114 and removed therefrom, the semi-spherical outer surface portion 310 in the third embodiment is formed with a notch 312 that allows the semi-spherical outer surface portion 310 to be radially compressed under pressure to reduce its diameter enough to allow it to be passed through the distal opening (or, alternatively or additionally in other embodiments, the interior opening) of the curvate socket 114. Once the pressure is released, the semi-spherical outer surface portion 310 returns to its resting diameter. Therefore, a force can be applied to press the semi-spherical outer surface portion 310 through the distal opening of the curvate socket 114, causing the semi-spherical outer surface portion 310 to radially compress enough to pass through the distal opening. Once through the distal opening, the radially pressure is alleviated and the semi-spherical outer surface portion 310 returns to its resting diameter, and therefore it is secured loosely within the curvate socket 114 to that it can rotate therein without slipping out. Of course, if it is desirable to then remove the semi-spherical outer surface portion 310 from the curvate socket 114, a force can again be applied to press the semi-spherical outer surface portion 310 through the distal opening of the curvate socket 114 (for example, by applying pressure against the proximal end 306 of the collet shaft 302).

The drill bit can easily be inserted into and rotated within the longitudinal bore 308 as necessary during a drilling procedure.

The drill guide body 100 has a handle 108 that can be gripped by a surgeon and used to fix the drill guide body 100 in relation to the target area to be drilled, as the drill guide collet shaft 302 is manipulated relative to the drill guide body 100 to angle the longitudinal bore 308 of the drill guide collet 300 to a desired drilling angle. In the illustrated example, the fixation of the drill guide body 100 to the target area is provided in that the target area to be drilled is below a plate 400, and the plate 400 includes a hole 402 through which a screw (not shown) is to be screwed into the target area. Accordingly, in this third embodiment of the present invention, the drill guide body 100 has a distal end 110 with an outer surface 112 that is formed to rigidly engage the hole 402 of the plate 400 so that the narrow end 104 of the conical bore 102 can be maintained adjacent the target area. This rigid engageability is provided inasmuch as the distal end 110 of the drill guide body 100 has a portion 116 of its outer surface 112 that fits within the hole 402 such that the narrow end 104 of the conical bore 102 is in communication with the target area, and a portion 118 of its outer surface 112 that cannot fit within the hole 402 and prevents passage of the fitting portion 116 through the hole 402.

Preferably, as shown, the fitting portion 116 is dimensioned to prevent lateral movement of the fitting portion 116 within the hole 402. It should be noted that the present invention can be adapted for use with any hole formation, including circular, oblong, square, rectangular, or other shaped holes. Further the distal end 110 of the drill guide body 100 can be formed to match the shape of the particular hole, with the fitting portion 116 having dimensions slightly smaller than the hole dimensions (so that it can fit within the hole with limited or no lateral movement therein), and the non-fitting portion 118 having dimensions greater than the hole dimensions. For example, in the case of a circular hole having a hole diameter, the outer surface 112 of the distal end 110 of the drill guide body 100 would have an annular recess establishing a diameter of the fitting portion 116 that is slightly smaller than the hole diameter, and a diameter of the non-fitting potion 118 that is larger than the hole diameter. Or, for example, in the case of an oblong hole (or other shaped hole), the outer surface 112 of the distal end 110 of the drill guide body 100 would have a recess shaped to establish a shape of the fitting portion 116 that matches the shape of the hole (but slightly smaller so that it fits in the hole), and to establish at least one dimension of the non-fitting portion 118 that is larger than a corresponding dimension of the hole 402.

In other embodiments, the distal end 110 of the drill guide body 100 can be formed to enable some lateral movement of the fitting portion 116 within the hole 402. Such embodiments can be used where the hole presents not one target area, but rather a region presenting many possible target areas. For example, the hole 402 can be an oblong hole having a particular length, and the fitting portion 116 can be formed to have the dimensions of a circle fitting within the oblong hole, or the dimensions of an oval fitting within the oblong hole (but with a length shorter than the length of the oblong hole). Such a fitting portion 116 formation would enable the fitting portion 116 to be moved laterally within the hole 402, along the length of the oblong hole, so that even after the plate 400 is held in place, further determinations can be made as to the desirable place for the drill hole. Particular formations of the hole edges and/or the fitting portion edges can be used to ease the lateral movement; such formations can be tracks, rails, or the like. Lateral movement in more than one linear axis can be achieved as well, using, for example, cross-shaped holes, t-shaped holes, or holes having tracks or grids spanning the hole and upon which the fitting portion rides to be placed in a plurality of positions.

Further, the longitudinal bore 308 of the drill guide collet 300 has a formation 318 at the proximal end 306 of the drill guide collet shaft 302 that facilitates the insertion of a drill bit into the longitudinal bore 308. This formation 312 is provided inasmuch as the longitudinal bore 308 is outwardly tapered at the proximal end 306 of the drill guide collet shaft 302 50 that insertion of the drill bit into the relatively wider tapered end of the longitudinal bore 308 guides the drill bit into the relatively narrower main portion of the longitudinal bore 308. It should be understood that other formations can be used alternatively to achieve a similar result.

Figures 4A, 4B:
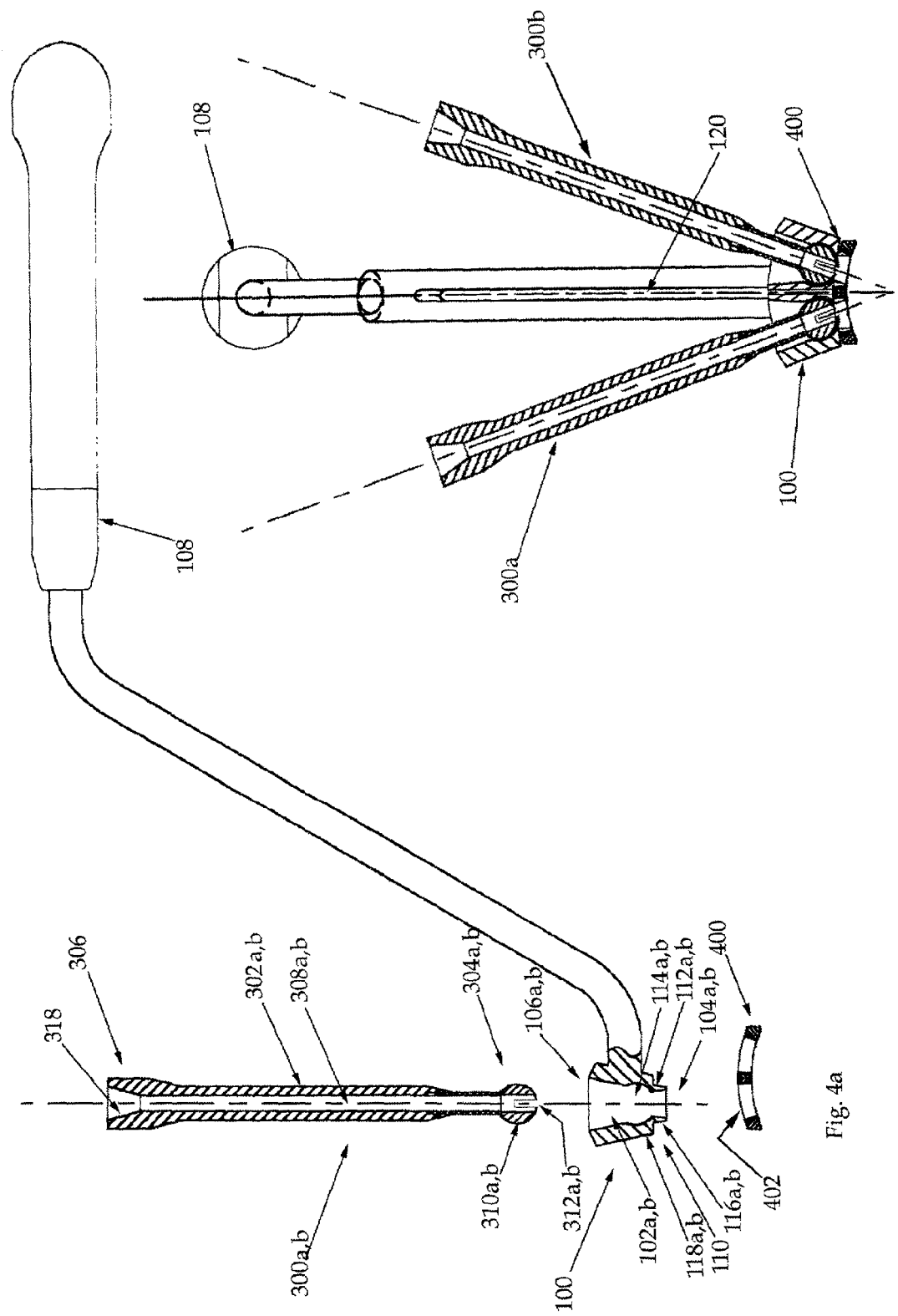
FIG. 4a is a side exploded view of a fourth embodiment of the present invention, showing a dual polyaxial drill guide having a drill guide body with two curvate sockets (one socket is behind the other in this view) and two drill guide collets with curvate heads (one collet is behind the other in this view).
FIG. 4b is a front assembled view of the fourth embodiment of the present invention, engaging a cervical plate, with each drill guide collet longitudinal bore coaxial with a respective conical bore of the drill guide body.

Referring now to FIGS. 4a–b, a fourth embodiment of the present invention is shown as similar to the third embodiment, but having a plurality of (in this example, two; it should be understood that more than two can be provided within the scope of the present invention) guide channels (each guide channel being established by a drill guide collet) rather than a single guide channel as in the third embodiment. Accordingly, this fourth embodiment includes a drill guide body 100 and two drill guide collets 300a, 300b (also referred to herein as guide members).

Each of the drill guide collets 300a, 300b includes a collet shaft 302a, 302b having a distal end 304a and a proximal end 306a, 306b and a longitudinal bore 308a, 308b having a diameter that accommodates a drill bit. The drill guide body 100 includes two conical bores 102a, 102b, each having a narrow end 104a, 104b and a wide end 106a, 106b. Each collet shaft distal end 304a, 304b rotatably mounts within the associated conical bore narrow end 104a, 104b, with its collet shaft 302a, 302b extending toward the associated conical bore wide end 106a, 106b, such that its collet shaft 302a, 302b (and consequently the associated longitudinal bore 308a, 308b) can be angled within the associated conical bore 102a, 102b at a plurality of angles with respect to the major axis of the associated conical bore 102a, 102b. The conical angle of each conical bore 102a, 102b establishes the extent to which the associated collet shaft 302a, 302b can be angled.

The rotatable mounting is provided inasmuch as each conical bore narrow end 104a, 104b has a socket 114a, 114b and each collet shaft distal end 304a, 304b has a semi-spherical outer surface 310a, 310b. Each semi-spherical outer surface portion 310a, 310b seats within the associated socket 114a, 114b and can rotate therein when so fitted. In this fourth embodiment, the walls of each socket 114a, 114b have a curvature that matches the contour of the associated semi-spherical outer surface portion 310a, 310b; however, it should be understood that in other embodiments, walls of other types can be used, such as, for example, walls having a different curvature. Also in this fourth embodiment, each semi-spherical outer surface portion 310a, 310b cannot be placed into or removed from the associated socket 114a, 114b without the application of force. For example, each socket 114a, 114b is curvate (preferably, as shown, ball-shaped) and the resting diameter of each semi-spherical outer surface portion 310a, 310b is greater than the distal opening of the associated curvate socket 114a, 114b, and greater than the interior opening (also referred to herein as the proximal opening) of the associated curvate socket 114a, 114b. This prevents each semi-spherical outer surface portion 310a, 310b from slipping out of the associated curvate socket 114a, 114b once it is fitted therein.

In order to enable each semi-spherical outer surface portion 310a, 310b to be seated in the associated curvate socket 114a, 114b and removed therefrom, each semi-spherical outer surface portion 310a, 310b in the fourth embodiment is formed with a notch 312a, 312b that allows the semi-spherical outer surface portion 310a, 310b to be radially compressed under pressure to reduce its diameter enough to allow it to be passed through the distal opening (or, alternatively or additionally in other embodiments, the interior opening) of the associated curvate socket 114a, 114b. Once the pressure is released, the semi-spherical outer surface portion 310a, 310b returns to its resting diameter. Therefore, a force can be applied to press each semi-spherical outer surface portion 310a, 310b through the distal opening of the associated curvate socket 114a, 114b, causing the semi-spherical outer surface portion 310a, 310b to radially compress enough to pass through the associated distal opening. Once through the associated distal opening, the radially pressure is alleviated and the semi-spherical outer surface portion 310a, 310b returns to its resting diameter, and therefore it is secured loosely within the associated curvate socket 114a, 114b so that it can rotate therein without slipping out. Of course, if it is desirable to then remove either semi-spherical outer surface portion 310a, 310b from the associated curvate socket 114a, 114b, a force can again be applied to press the semi-spherical outer surface portion 310a, 310b through the distal opening of the associated curvate socket 114a, 114b (for example, by applying pressure against the appropriate collet shaft proximal end 306a, 306b).

The drill bit can easily be inserted into and rotated within either longitudinal bore 308a, 308b as necessary during a drilling procedure.

The drill guide body 100 has a handle 108 that can be gripped by a surgeon and used to fix the drill guide body 100 in relation to the target areas to be drilled, as each collet shaft 302 is manipulated relative to the drill guide body 100 to angle each collet shaft longitudinal bore 308a, 308b to a respective desired drilling angle. In the illustrated example, the fixation of the drill guide body 100 relative to the target areas is provided in that the target areas to be drilled are below a plate 400, and the plate 400 includes two holes 402a, 402b through which respective screws (not shown) are to be screwed into the respective target areas. Accordingly, in this fourth embodiment of the present invention, the drill guide body 100 has a distal end 110 with two outer surfaces 112a, 112b that are formed to rigidly engage a respective one of the holes 402a, 402b of the plate 400 so that the conical bore narrow ends 104a, 104b can be maintained adjacent the respective target areas. This rigid engageability is provided inasmuch as each of the distal end outer surfaces 112a, 112b has a portion 116a, 116b that fits within the respective one of the holes 402a, 402b such that the associated conical bore narrow end 104a, 104b is in communication with the respective target area, and a portion 118a, 118b that cannot fit within the respective one of the holes 402a, 402b and prevents passage of the fitting portions 116a, 116b through the respective one of the holes 402a, 402b.

Preferably, as shown, each fitting portion 116a, 116b is dimensioned to prevent lateral movement thereof within the respective hole 402a, 402b. It should be noted that the present invention can be adapted for use with any hole formation, including circular, oblong, square, rectangular, or other shaped holes. Further, the distal end 110 of the drill guide body 100 can be formed to match the shape of the particular hole, with each fitting portion 116a, 116b having dimensions slightly smaller than the respective hole dimensions (so that it can fit within the hole with limited or no lateral movement therein), and the non-fitting portion 118a, 118b having dimensions greater than the respective hole dimensions. For example, in the case of a circular hole having a hole diameter, each distal end outer surface 112a, 112b would have an annular recess establishing a diameter of the associated fitting portion 116a, 116b that is slightly smaller than the respective hole diameter, and a diameter of the associated non-fitting potion 118a, 118b that is larger than the respective hole diameter. Or, for example, in the case of an oblong hole (or other shaped hole), each distal end outer surface 112a, 112b would have a recess shaped to establish the shape of each fitting portion 116a, 116b that matches the shape of the respective hole (but slightly smaller so that it fits in the hole), and to establish at least one dimension of each non-fitting portion 118a, 118b that is larger than a corresponding dimension of the respective hole 402a, 402b.

In other embodiments, the distal end 110 of the drill guide body 100 can be formed to enable some lateral movement of one or more of the fitting portions 116a, 116b within the associated hole 402a, 402b. Such embodiments can be used where the hole presents not one target area, but rather a region presenting many possible target areas. For example, one or more of the holes can be an oblong hole having a particular length, and the associated fitting portion can be formed to have the dimensions of a circle fitting within the oblong hole, or the dimensions of an oval fitting within the oblong hole (but with a length shorter than the length of the oblong hole). Such a fitting portion formation would enable the fitting portion to be moved laterally within the hole, along the length of the oblong hole, so that even after the plate is held in place, further determinations can be made as to the desirable place for the drill hole. Particular formations of the hole edges and/or the fitting portion edges can be used to ease the lateral movement; such formations can be tracks, rails, or the like. Lateral movement in more than one linear axis can be achieved as well, using, for example, cross-shaped holes, t-shaped holes, or holes having tracks or grids spanning the hole and upon which the fitting portion rides to be placed in a plurality of positions.

It should be noted that each conical bore 102a, 102b is formed in a respective portion of the drill guide body 100, and that the portions are movable relative to one another. This enables this embodiment of the present invention to accommodate a variety of hole spacings on plates. For example, one plate with which this embodiment is used may have holes that are spaced apart by a particular distance, whereas another plate with which this embodiment is used may have holes that are slightly closer together, slightly farther apart, or otherwise not in the same configuration as the first plate. Because the portions of the drill guide body 100 are movable relative to one another, the embodiment can adjust to the different plate configurations; this prevents the surgeon from having to use a different drill guide for each plate. In this embodiment, the relative movability is provided inasmuch as the portions of the body are separated from one another by a slot 120 formed in the body. The slot 120 is formed to allow the connected regions of the body to act as a fulcrum point for the portions moving relative to one another about the fulcrum point. It should be understood that the relative movability can be provided in other ways without departing from the scope of the invention, including through the use of hinges, joints, and the like. It should also be understood that if more than two portions are required to be made movable relative to one another, that additional slots (or hinges, or joints, or the like) can be provided in the drill guide body 100 to effect this.

Further, each collet shaft longitudinal bore 308a, 308b has a formation 318a, 318b at the collet shaft proximal end 306a, 306b that facilitates the insertion of a drill bit into the longitudinal bore 308a, 308b. Each formation 312a, 312b is provided inasmuch as the associated longitudinal bore 308a, 308b is outwardly tapered at the associated collet shaft proximal end 306a, 306b so that insertion of the drill bit into either longitudinal bore's relatively wider tapered end guides the drill bit into the relatively narrower main portion of the associated longitudinal bore 308a, 308b. It should be understood that other formations can be used alternatively to achieve a similar result.

Figure 5:
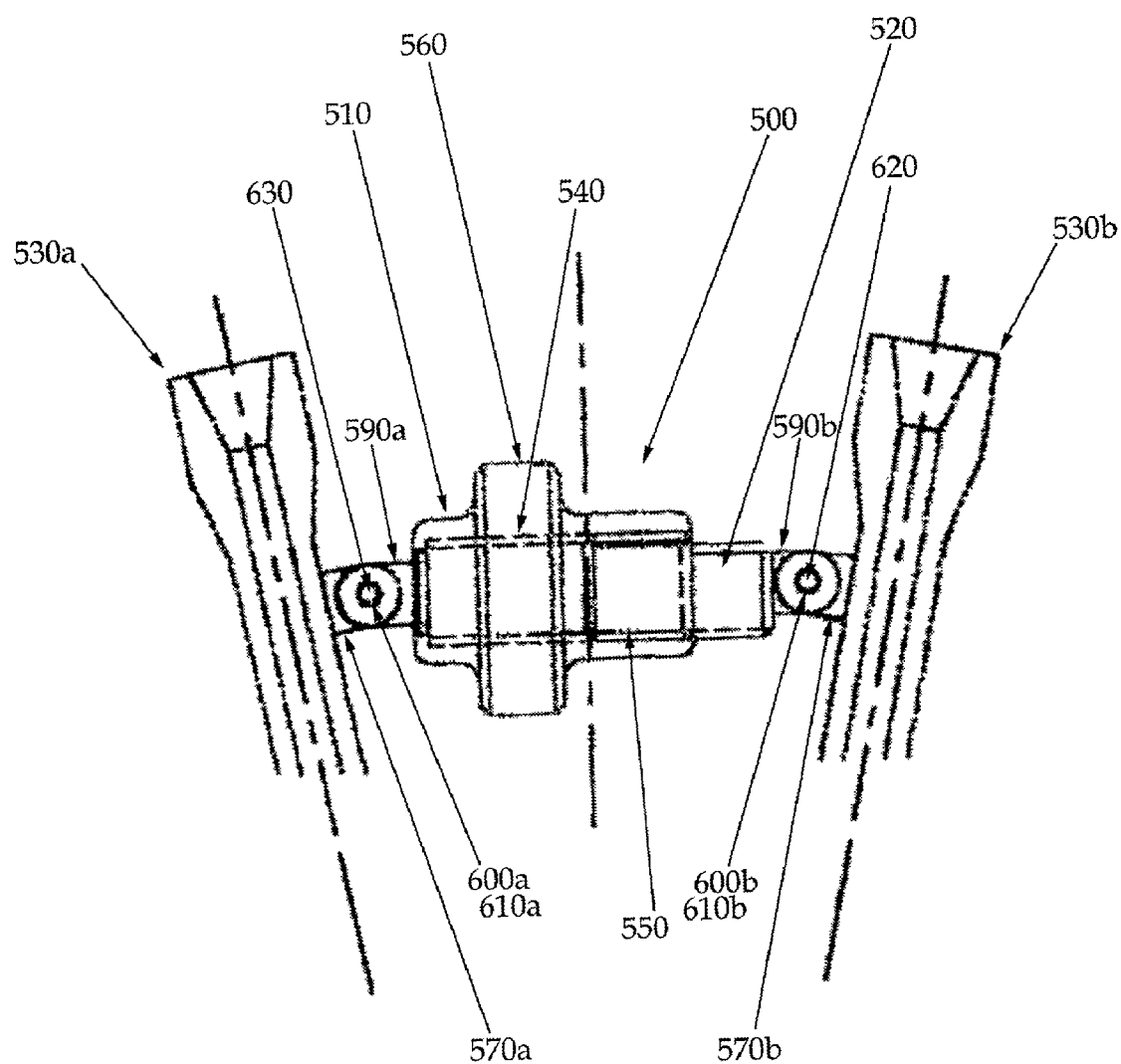
FIG. 5 is a front view of a link between two guide members of the present invention.

Referring now to FIG. 5, a link between two exemplary guide members 530a, 530b of the present invention is shown as one example of a link that can be used with the present invention. It should be understood that in other embodiments more than two guide members can be linked for mutual relative angulation. It should also be understood that while a particular mechanical link is shown, other mechanical and non-mechanical links (such as, for example, electronic- or computer-based links), can also or alternatively be used. The illustrated link is a turnbuckle 500 that has a first member 510 moving relative to a second member 520. In this example, the movement is linear and the movement is effected by cooperating threaded portions on each of the members 510, 520, the first member 510 having a threaded bore 540 and the second member 520 having an outer threading 550. Rotation of one of the members 510, 520 relative to the other causes the threaded portions 540, 550 to engage and move the members 510, 520 linearly relative to one another (as denoted by the directional arrows on FIG. 5). For example, an operator can grip a knurled portion 560 on the first member 510 and rotate the first member 510 relative to the second member 520. Each of the members 510, 520 is secured to a respective one of the guide members 530a, 530b. Preferably, as shown, the securing is accomplished by protrusions 570a, 570b on the guide members 530a, 530b, and protrusions 590a, 590b on the first and second turnbuckle members 510, 520. Each of the protrusions has a bore 600a, 600b, 610a, 610b, through which pins 620, 630 are placed so that the guide members 530a, 530b are free to angulate with respect to the turnbuckle 500. Preferably, the pins 620, 630 can be optionally removed if desired so that the guide members 530a, 530b can be angulated independently. It should be understood that in other embodiments, other securing mechanisms can be used. In operation, when it is desirable to angulate the guide members 530a, 530b relative to one another, for example, to cause the angle of each guide member relative to the drill guide body to be roughly equivalent to the angle of the other guide member relative to the drill guide body, the pins 620, 630 can be placed through the bores 600a, 600b, 610a, 610b, and the turnbuckle 500 can be actuated (e.g., by turning the first member 510 relative to the second member 520) to increase or decrease the angle between the guide members 530a, 530b.

While there has been described and illustrated specific embodiments of a polyaxial drill guide, it will be apparent to those skilled in the art that variations and modifications are possible without deviating from the broad spirit and principle of the present invention. The invention, therefore, shall not be limited to the specific embodiments discussed herein.

We claim:

1. A drill guide, comprising:
a body having a conical bore, the conical bore having a major axis and a wide end and a narrow end and a socket formed near the narrow end, the socket having a proximal opening leading into the conical bore and a distal opening opposite the proximal opening;
a guide member having a shaft having a distal end and a proximal end and a longitudinal bore, the distal end having a semi-spherical outer surface portion through which the longitudinal bore extends; wherein
the shaft of the guide member extends through the proximal opening and towards the wide end of the conical bore and the semi-spherical outer surface portion is rotatably mounted within the socket so that the guide member shaft is angulatable at a plurality of angles with respect to the major axis of the conical bore.

2. The drill guide of claim 1, further comprising an extension member having a shaft having a distal end and a proximal end and a longitudinal bore, wherein the distal end of the extension member shaft is mounted to the proximal end of the guide member shaft such that the longitudinal bore of the guide member shaft and the longitudinal bore of the extension member shaft are co-linear.

3. The drill guide of claim 2, wherein the mounting is provided by an outer threading on one of the distal end of the extension member shaft and the proximal end of the guide member shaft, and an inner threading on the other of the distal end of the extension member shaft and the proximal end of the guide member shaft, the inner threading matching the outer threading for mutual engageability.

4. The drill guide of claim 2, wherein the distal end of the extension member shaft is provided with a conformation that confronts the body near the wide end of the conical bore so as to limit movement of the extension member shaft toward the narrow end of the conical bore.

5. The drill guide of claim 4, wherein the conformation includes at least one flange.

6. The drill guide of claim 4, wherein the diameter of the semi-spherical outer surface portion is greater than the proximal opening of the socket so as to prevent movement of the semi-spherical surface portion into the conical bore.

7. The drill guide of claim 1, wherein the semi-spherical outer surface portion has a contour and the socket has at least one curvate wall following at least a portion of the contour of the semi-spherical outer surface portion.

8. The drill guide of claim 7, wherein the socket is a ball-shaped socket having a diameter greater than the distal opening and greater than the proximal opening, and wherein the diameter of the semi-spherical outer surface portion is greater than the distal opening and greater than the proximal opening so as to prevent movement of the semi-spherical outer surface portion out of the socket.

9. The drill guide of claim 8, wherein the semi-spherical outer surface portion is radially compressible so as to be passable through at least one of the openings of the socket.

10. The drill guide of claim 9, wherein the semi-spherical outer surface portion has a slot that allows the semi-spherical outer surface portion to be radially compressed.

* * * * *